US011519889B2

(12) United States Patent
Yamamoto

(10) Patent No.: US 11,519,889 B2
(45) Date of Patent: Dec. 6, 2022

(54) BIOLOGICAL SAMPLE AUTOMATIC ANALYSIS SYSTEM

(71) Applicant: Shimadzu Corporation, Kyoto (JP)

(72) Inventor: Kohei Yamamoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 236 days.

(21) Appl. No.: 16/756,044

(22) PCT Filed: Dec. 5, 2017

(86) PCT No.: PCT/JP2017/043589
§ 371 (c)(1),
(2) Date: Apr. 14, 2020

(87) PCT Pub. No.: WO2019/111311
PCT Pub. Date: Jun. 13, 2019

(65) Prior Publication Data
US 2020/0309747 A1 Oct. 1, 2020

(51) Int. Cl.
*G01N 30/72* (2006.01)
*G01N 27/62* (2021.01)
(Continued)

(52) U.S. Cl.
CPC .............. *G01N 30/72* (2013.01); *G01N 27/62* (2013.01); *G01N 30/86* (2013.01); *G01N 35/00871* (2013.01)

(58) Field of Classification Search
CPC .......... G01N 35/025; G01N 35/00722; G01N 35/00623; G01N 35/0095; G01N 35/00871; G01N 35/0092; G01N 2035/009; G01N 2035/0091; G01N 2035/00891
See application file for complete search history.

(56) References Cited

U.S. PATENT DOCUMENTS

| 2013/0009988 A1* | 1/2013 | Tokunaga | G01N 35/00871 345/660 |
| 2017/0052171 A1* | 2/2017 | Suzuki | G01N 33/5005 |
| 2019/0119650 A1 | 4/2019 | Suzuki et al. | |

FOREIGN PATENT DOCUMENTS

| CN | 102483423 A | 5/2012 |
| CN | 106460028 A | 2/2017 |

(Continued)

OTHER PUBLICATIONS

LC/MS/MS Method Package Cell Culture Profiling, [online], [Searched on Nov. 21, 2017], Shimadzu Corporation, Internet, with a machine translation.

(Continued)

*Primary Examiner* — David E Smith
*Assistant Examiner* — Hsien C Tsai
(74) *Attorney, Agent, or Firm* — Muir Patent Law, PLLC

(57) ABSTRACT

A display control unit (52) displays a screen for setting sample information on a display unit (8) for each sample placed in a sample placement section (20), and an input processing unit (53) receives information such as a culture name and seeding date and time information input by an operator via an operation unit (7), and stores the information in a storage unit (55). This file is transferred to a data processing unit (4) and stored in a sample information storage unit (40). After analyzing the respective samples in an LC-MS (3), a quantitative analysis unit (42) performs a quantitative analysis based on the obtained data, associates the analysis result with the sample information, and stores the data in an analysis result storage unit (43). As a result, the sample information and the analysis result of the respective samples in the preprocessing stage are associated with each other. Result display processing unit (44) arranges sample information and an analysis result for one sample on the same screen and displays them on display unit (8). With (Continued)

this display, an operator can easily and accurately grasp the correspondence relationship between the sample information and the analysis result of a plurality of sample to be subjected to preprocessing.

8 Claims, 12 Drawing Sheets

(51) Int. Cl.
*G01N 30/86* (2006.01)
*G01N 35/00* (2006.01)

(56) References Cited

FOREIGN PATENT DOCUMENTS

| | | |
|---|---|---|
| EP | 2485054 A1 | 8/2012 |
| EP | 3138922 A1 | 8/2017 |
| JP | 2016-170079 A | 9/2016 |
| JP | 2017-170079 A | 9/2019 |
| KR | 10-2016-0143804 A | 12/2016 |
| WO | 2011/037069 A1 | 3/2011 |
| WO | 2015/166845 A1 | 5/2015 |
| WO | 2017/068727 A1 | 4/2017 |
| WO | 2017/068801 A1 | 4/2017 |

OTHER PUBLICATIONS

SCLAM-2000 Fully Automated LCMS preprocessing device, [online], [Search on Nov. 21, 2017], Shimadzu Corporation, Internet, with a partial translation.
"LabSolutions LCMS to Support Efficient Workflow Building", [online], [Searched on Nov. 24, 2017] Shimadzu Corporation, Internet, with a machine translation.
Written Opinion of the International Searching Authority (ISA237) for PCT application No. PCT/JP2017/043589, dated Feb. 20, 2018, submitted with a machine translation.

* cited by examiner

FIG. 4

BIOLOGICAL SAMPLE AUTOMATIC ANALYSIS SYSTEM

TECHNICAL FIELD

The present invention relates to a biological sample automatic analysis system for performing predetermined preprocessing on a sample derived from a living organism and analyzing the preprocessed sample. The biological sample described herein denotes a sample containing a compound derived from a living organism, and includes whole blood, sera, filter paper blood, urine, and the like, as well as culture supernatant containing compounds, such as, e.g., various kinds of cells such as pluripotent stem cells and various metabolites obtained from a culture medium for culturing microorganisms.

BACKGROUND OF THE INVENTION

In the field of regenerative medicine, researches and technological developments using pluripotent stem cells, such as, e.g., iPS cells and ES cells, have been actively carried out in recent years. In such researches and technological developments, it is necessary to culture a large quantity of undifferentiated cells in a state in which pluripotency is maintained. Therefore, it is necessary to select an appropriate cultural environment and stably control the environment, and it is also necessary to confirm the state of cells in culture at a high frequency.

For example, if cells within a cell colony deviate from a differentiation state, all cells within the cell colony will eventually transition to an undifferentiated deviant state because all cells within the cell colony are capable of differentiating. Therefore, the operator needs to check on a daily basis whether or not cells that deviate from a differentiation state (cells that have already differentiated or are likely to differentiate) are generated in the cultured cells, that is, the differentiation state of the cells.

Conventionally, as a method for evaluating the differentiation state of cells, a method using immunostaining or a method for quantifying the expression level of a marker gene has been widely used. However, all of these methods require an invasive treatment of the cells. Therefore, it was not possible to use the cells used for the evaluation after the evaluation of the differentiation state for another purpose, for example, as a cell source for regenerative medicine. It was also impossible to evaluate changes over time for the completely identical sample.

On the other hand, Patent Documents 1 to 3 disclose a method in which, not a cell itself, but the abundance of a particular compound in a culture supernatant of a culture medium culturing cells is analyzed using a liquid chromatograph mass spectrometer (LC-MS), a gas chromatograph mass spectrometer (GC-MS) or the like, and the differentiation state of the cells is evaluated based on the result. To perform such a method, software for an LC-MS to perform an analysis of a culture medium culturing cells has also been put into practical use (see Non-Patent Document 1). Such a method has a significant benefit that the differentiation state of cells can be assessed non-invasively with respect to the cells.

When evaluating a differentiation state of cells based on an analysis result of a particular compound in a culture supernatant as described above, after a sample cell is cultured in a culture medium, a sample (culture medium sample) derived from a culture medium used for the culture is introduced from a culturing device to an analysis device such as an LC-MS. Note that the culture medium sample also includes proteins or the like which are not necessary for evaluating the differentiation state of the cells and which may denature the target compound over time. For this reason, generally, a culture medium sample after a preprocessing such as removing proteins in a preprocessing device has been performed is introduced into an LC-MS. That is, a culture medium sample is introduced from a culturing device to an analysis device such as an LC-MS via a preprocessing device. As a preprocessing device, a device capable of automatically and sequentially processing a large number of samples accommodated in sample containers, which is disclosed in Patent Document 4, Non-Patent Document 2, and so on, is usable.

As disclosed in Patent Document 4, etc., the above-mentioned preprocessing device has a configuration in which one of a number of sample containers placed in a sample placement section in advance is selected, predetermined preprocessing is performed on a sample accommodated in the sample container, and the container accommodating the processed sample is transferred to a position where the next analysis device can handle the container. In cases where a batch analysis is performed in which a large number of samples are sequentially analyzed by an analysis device such as an LC-MS after preprocessing of a large number of samples has been performed in such a preprocessing device, a large number of sample containers accommodating preprocessed samples are placed in a sample placement section of an auto-sampler for selecting one of a large number of samples in an LC-MS and introducing it to an LC-MS. That is, a large number of sample containers are placed in a sample placement section of a preprocessing device, while a large number of sample containers are also placed in a sample placement section of an auto-sampler of an LC-MS.

A main body of the LC-MS is controlled by a computer in which, for example, software dedicated to an LC-MS control and data processing as disclosed in Non-Patent Document 3 and a method package for a multicomponent simultaneous analysis specialized for a particular purpose as disclosed in Non-Patent Document 1 are introduced, and the data collected by the analysis is processed. With this, it is possible to obtain a quantitation result of multiple components for each sample prepared in advance in an auto-sampler.

PRIOR ART DOCUMENT

Patent Document

Patent Document 1: International Publication WO2015/166845
Patent Document 2: International Publication WO 2017/068727
Patent Document 3: International Publication WO 2017/068801
Patent Document 4: Japanese Unexamined Patent Application Publication No. 2017-170079

Non-Patent Document

Non-Patent Document 1: LC/MS/MS Method Package Cell Culture Profiling, [online], [Searched on Nov. 21, 2017], Shimadzu Corporation, Internet <URL: http://www.an.shimadzu.co.jp/lcms/tq-option/mp_profiling_cell-culture.htm>

Non-Patent Document 2: SCLAM-2000 Fully Automated LCMS preprocessing device, [online], [Search on Nov. 21, 2017], Shimadzu Corporation, Internet <URL: http://www.an.shimadzu.co.jp/lcms/sclam2000-2.htm>

Non-Patent Document 3: "Lab Solutions LCMS to Support Efficient Workflow Building", [online], [Searched on Nov. 24, 2017], Shimadzu Corporation, Internet <URL: http://www.an.shimadzu.co.jp/lcms/lcmsms_methodpac page.htm>

SUMMARY OF THE INVENTION

Problems to be Solved by the Invention

Particularly, in the case of stably culturing a large quantity of cells, it is required to evaluate the differentiation status of a sample cell in a culture by continuously analyzing a culture supernatant in one cultivation container of a seeding date and time, for example, daily at the same time (or every predetermined time elapse), without delay until the end of the culture. In such analyses, a culture medium sample with the same culture name (i.e., derived from one culture container) is analyzed, for example, on time every day, and the respective data files and analysis result files are created and stored. Since the amount of a compound (e.g., a metabolites by cells) in a culture medium sample derived from the same cultivation container varies from day to day, it is essential to grasp the temporal variations, such as the amount of a given compound in a sample having a single culture name, based on a plurality of data files and analysis result files stored daily.

However, in a conventional system in which a preprocessing device and an LC-MS are combined, since only the association between a culture medium sample to be analyzed by the LC-MS and a data file or an analysis result file obtained for the sample is considered, it is difficult to manage the data so as to associate a plurality of series of analysis results with one culture name as described above.

Particularly in the case of a cell culture, the amount of metabolites in a culture medium may change due to slight differences in seeding date and time and collection date and time, etc., and therefore the analysis result may be affected. For this reason, the analysis result needs to be evaluated based on the culture name including the information such as the seeding date and time and the collection date and time. However, a conventional system does not cope with such an evaluation method.

The present invention has been made to solve the aforementioned problems. An object of the present invention is to provide a biological sample automatic analysis system capable of easily and accurately grasping a correspondence relationship between information of a sample to be subjected to preprocessing and a plurality of analysis results by an operator.

Means for Solving the Problem

The present invention made to solve the above-mentioned problems relates to a biological sample automatic analysis system in which predetermined preprocessing is performed on a sample derived from a living organism and then a predetermined analysis is performed on the sample that has been subjected to the preprocessing, includes:

a) a preprocessing device having a first sample placement section for placing a plurality of sample containers each accommodating a sample, the preprocessing device being configured to perform preprocessing on the sample in the sample container placed in the first sample placement section;

b) an analysis device having a second sample placement section for placing a plurality of sample containers each accommodating the sample that has been subjected to the preprocessing by the preprocessing device, the analysis device being configured to perform an analysis on the sample that has been subjected to the preprocessing in the sample container placed in the second sample placement section;

c) a sample information acquisition unit configured to acquire sample information related to the sample accommodated in each sample container placed in the first sample placement section in association with a sample container identifier assigned to each sample container according to a placement position in the first sample placement section;

d) a sample container identifier management unit configured to manage a sample container identifier assigned to each sample container depending on a placement position in the first sample placement section and a sample container identifier assigned to each sample container depending on a placement position in the second sample placement section, the sample container identifier assigned to the sample container in the first sample placement section being the same as the sample container identifier assigned to the sample container in the second sample placement section; and e) an analysis result storage processing unit configured to receive sample information obtained by the sample information acquisition unit and store an analysis result obtained by an analysis by the analysis device on a sample in a sample container to which an arbitrary sample container identifier has been assigned, with or in association with sample information corresponding to the sample container identifier, in accordance with a management by the sample container identifier management unit.

The analytical method in the analysis device according to the present invention is not particularly limited, but the analysis device is, for example, a liquid chromatograph (LC), a gas chromatograph (GC), a liquid chromatograph mass spectrometer (LC-MS), or a gas chromatograph mass spectrometer (GC-MS). Further, the contents of the preprocessing in the preprocessing device are not particularly limited, but may be, for example, a process for removing various components, such as proteins, which may hinder the analysis. The biological sample described herein is sometimes a sample itself collected from a living body such as blood, but may be a culture medium sample containing components derived from cells described above or living tissues when culturing the same.

In the present invention, prior to the analysis, a plurality of sample containers each accommodating a biological sample such as a culture medium sample are prepared in the first sample placement section. The sample container is, for example, a vial. In this case, the first sample placement section is, for example, a rack in which a recess is formed in which a bottom of a vial is accommodated. When the preprocessing is started, the preprocessing device sequentially executes the preprocessing on samples in the prepared sample containers. For example, a sample in which the preprocessing has been completed is once accommodated in a container different from a sample container, and the container is transferred to a predetermined position of the analysis device.

In the analysis device, a predetermined quantity of the preprocessed sample is aspirated from the container transferred to the predetermined position and injected into a sample container (a sample container different from the sample container used for the preprocessing) placed in the second sample placement section. At this time, dilution or the like may be performed. By repeating this operation, in the sample containers placed in the second sample placement section, preprocessed samples different from each other are accommodated. The analysis device sequentially analyzes the preprocessed samples in the sample containers and acquires an analysis result for each sample. For example, in cases where the analysis device is an LC-MS, the analysis result may be extracted ion chromatogram data (also referred to as a mask chromatogram) of a predetermined time range in one or a plurality of mass-to-charge ratios, or a quantitative value of each compound calculated based on the chromatogram.

The sample information acquisition unit displays, for example, a sample information setting screen in a predetermined format on the display unit, and acquires textual information or the like input by predetermined operations by an operator on the screen as sample information. The sample information may be input for each placement position of the sample container in the first sample placement section, that is, for each sample container placed in the placement position, in association with the sample container identifier. Alternatively, the sample information may be input collectively to a plurality of sample containers.

In the present invention, in cases where the biological sample is a culture medium sample derived from a culture medium in which the sample cells are cultured, the sample information may include at least the culture name for specifying the culture medium and the seeding date and time of the cells. It is further preferable to include identifiers such as culture plate numbers and collection date and time of the culture medium sample for specifying the culture plate having the same culture name. It should be noted that although sample information is generally acquired by the sample information acquisition unit before the analysis is started, even if the sample information is unknown, the preprocessing and the analysis can be executed, and therefore, the acquisition of the sample information may be performed in the middle of the analysis or after the analysis is finished.

The sample container identifier management unit manages the relationship between a placement position and an identifier for a sample container identifier of each sample container placed in the first sample placement section and a sample container identifier of each sample container placed in the second sample placement section, both the identifiers being assigned so that the same identifier is assigned to samples derived from the same sample. The analysis result storage processing unit uses the management information of the identifier, receives the sample information acquired by the sample information acquisition unit, and stores the analysis result of the sample in the sample container to which an arbitrary sample container identifier is assigned, together with sample information corresponding to the sample container identifier or in association with each other in the storage unit. That is, the analysis result and the sample information for one sample may be stored in the same file, or the analysis result and the sample information may be stored in different files and linked to each other. In any case, since the sample information and the analysis result are stored in correspondence with each other for each sample, it becomes easy to, for example, output an analysis result corresponding to particular sample information or refer to sample information of a sample in which a characteristic analysis result is obtained.

Further, in the present invention, it is preferable to further include a display processing unit configured to display the analysis result stored by the analysis result storage processing unit and the sample information corresponding to the analysis result on a same screen of a display unit.

With this configuration, an operator can check the sample information and the analysis result of one or a plurality of samples at a time on the screen of the display unit.

As one aspect of the present invention, it may be configured such that the analysis device includes a liquid chromatograph mass spectrometer or a gas chromatograph mass spectrometer, and the analysis result includes a quantitative value for one or a plurality of compounds as a result of performing a data-based quantitative analysis obtained by the liquid chromatograph mass spectrometer or the gas chromatograph mass spectrometer.

With this configuration, the analysis result of, e.g., a multicomponent simultaneous analysis of a sample can be displayed on a screen of the display unit.

Further, in the present invention, the sample information acquisition unit may be configured to create a file for storing the sample information associated with the sample container identifier, and register the sample information in a custom property of the file.

The property described herein is typically file attribute information defined in the OS (operating system) of Windows (registered trademark), and is information that can be read by a computer regardless of the data format of the file. The custom property is a property that allows a user to freely define the name and the value to some extent.

In general, in the field of a mechanical analysis, the data format of a file used for storing data and the like often differs depending on the specifications of the apparatus. Therefore, for example, if the manufacturer of a preprocessing device and the manufacturer of an analysis device differ from each other, the contents of the file in which sample information set corresponding to a sample container placed in the first sample placement section is stored cannot generally be read by the data-processing software in the analysis device.

On the other hand, in the biological sample automatic analysis system having the aforementioned configuration, since sample information is registered in the custom property, the sample information can be read out even under the data processing software provided by another manufacturer incompatible in data format. In this manner, according to this configuration, even in cases where the preprocessing device manufacturer and the analysis device manufacturer differ from each other, the sample information set corresponding to the sample container placed in the first sample placement section can be used in the data processing in the analysis device.

Effects of the Invention

According to the present invention, an operator can easily and accurately grasp the correspondence relationship between each sample information of a plurality of samples to be subjected to the preprocessing and the analysis result for each sample after the preprocessing. In addition, since the sample information such as the culture name and the plurality of analysis results are accurately linked, the analytical traceability can be improved.

BRIEF DESCRIPTION OF THE DRAWINGS

FIG. 4 is a diagram showing an example of property information of a culture medium sample in the culture medium sample automatic analysis system of this example.

EMBODIMENTS FOR CARRYING OUT THE INVENTION

Hereinafter, a culture medium sample automatic analysis system, which is an example of a biological sample automatic analysis system according to the present invention, will be described in detail with reference to the attached drawings.

Figure 1:
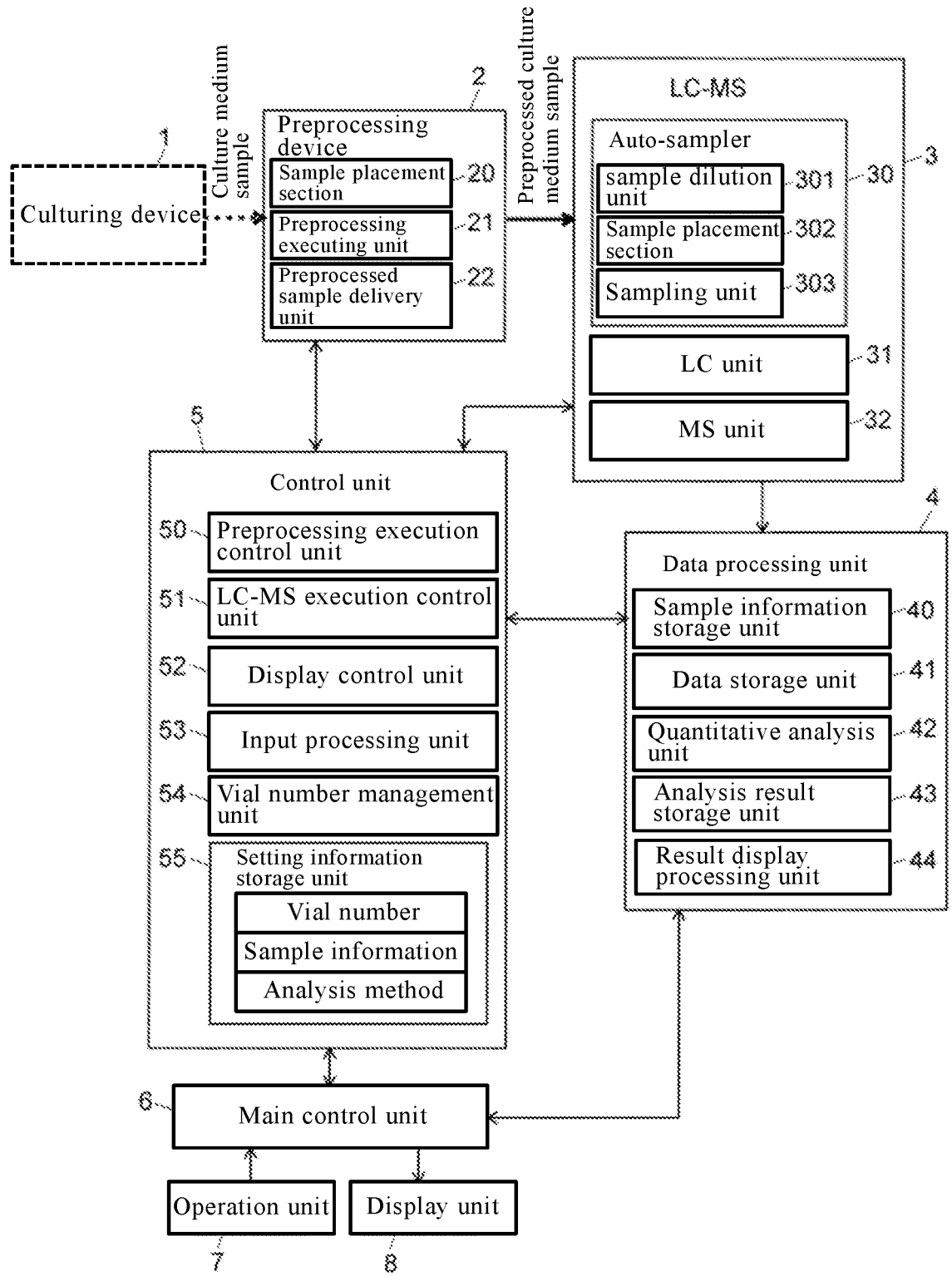
FIG. 1 is a schematic block configuration diagram of a culture medium sample automatic analysis system which is an example of the present invention.

FIG. 1 is a schematic block diagram of a culture medium sample automatic analysis system of this example. The system of this example is a cultured cell evaluation system that is used to assess the differentiation state of a sample cell based on the abundance of a biomarker (cellular metabolite) in a culture supernatant of a culture medium in which sample cells, such as pluripotent cells, are cultured.

The system of this example includes a preprocessing device 2, a liquid chromatograph mass spectrometer (LC-MS) 3, a data processing unit 4, a control unit 5, a main control unit 6, an operation unit 7, a display unit 8, etc. The culturing device 1 of the block indicated by the dotted line in FIG. 1 is not included in this system, and provides a culture medium sample to be analyzed in this system.

Schematically, in this system, a large number of culture medium samples obtained in the culturing device 1 are provided to the preprocessing device 2. In the preprocessing device 2, predetermined preprocessing is performed sequentially for a large number of culture medium samples. Then, each culture medium sample (preprocessed sample) that has been preprocessed by the preprocessing device 2 is sent to the LC-MS 3. The components in each culture medium sample are sequentially analyzed in the LC-MS 3. The data obtained by the analysis is sent to the data processing unit 4, and the data processing unit 4 performs a predetermined data process and outputs the result to the display unit 8 through the main control unit 6 for presentation to an operator. The control unit 5 controls the preprocessing device 2, the LC-MS 3, and the data processing unit 4 for such processes. The main control unit 6 mainly has a function as a user interface through the operation unit 7 and/or the display unit 8.

The configuration of each unit will be described in detail.

The culturing device 1 is a device for culturing sample cells. Here, the sample cells are, for example, stem cells, typically pluripotent stem cells, such as, e.g., ES cells or iPS cells. Cells differentiated from stem cells can also be used as sample cells. As a culture medium used for culturing such a sample cell, various culture mediums commonly used for culturing stem cells, such as DMEM/F12 or a culture medium (mTeSR1, etc.) containing DMEM/F12 as a main component, can be used. When cells are cultured on such a culture medium, various metabolites by cells are mixed in a culture supernatant. An operator prepares a culture medium sample by manually collecting a part of a culture supernatant and injecting it into a predetermined vial (sample container). Of course, a part of a culture supernatant may be automatically collected at a fixed time every day, i.e., a culture medium sample may be automatically prepared.

The preprocessing device 2 includes: a sample placement section 20 including a sample rack for placing a plurality of vials; a preprocessing execution unit 21 for performing preprocessing for removing unwanted components such as proteins through processes of sample dispensing, reagent dispensing, agitation, filtration, and the like, on a culture medium sample in one vial selected from a plurality of vials placed in the sample placement section 20; and a preprocessed sample delivery unit 22 for transferring a container in which a culture medium sample for which preprocessing has been completed is temporarily stored to a predetermined position of the LC-MS 3.

In this example, as will be described later, the sample rack used in the preprocessing device 2 has a substantially circular arc shape in a top view, and six pieces of sample racks are arranged in the sample placement section 20 along the circumferential direction of the circular ring. Ten or eleven vials can be placed in one sample rack. That is, each sample rack is provided with concave portions each having a size capable of accommodating a bottom of each of the plurality of vials. In each concave portion, a vial can be placed.

More specifically, in the preprocessing of removing proteins, isopropyl malic acid as an internal standard sample is added to a culture medium sample as a reagent, and can be processed with an extracting solution in which methanol, chloroform, and water are mixed in a ratio of 2.5:1:1, for example. However, the preprocessing is not limited to removal of proteins, and other preprocessing may be performed on a culture medium sample. As the preprocessing device 2, for example, a device disclosed in Patent Document 4, Patent Document 2, or the like can be used, but the present invention is not limited thereto.

The LC-MS 3 includes a liquid chromatograph (LC) unit 31 including a liquid feed pump, an injector, a column, and the like (not shown), an auto-sampler 30 for selecting one of a plurality of culture medium samples and introducing it into the LC unit 31, and a mass spectrometry (MS) unit 32 for performing mass spectrometry on components in a sample separated in a temporal direction by the column of the LC unit 31. The auto-sampler 30 includes a sample placement section 302 including a sample rack on which a number of vials differing from those used in the preprocessing device 2 are placed, a sample dilution unit 301 for aspirating a preprocessed culture medium sample in a container transferred to a predetermined position by the preprocessed sample delivery unit 22 of the preprocessing device 2, adding ultrapure water to dilute the container to a predetermined ratio, and then dispensing it into a vial placed in the sample placement section 302, and a sampling unit 303 for collecting a predetermined amount of a preprocessed and diluted culture medium sample from one of a plurality of vials placed in the sample placement section 302 and introducing the same into an injector of the LC unit 31.

In this example, as will be described later, the sample rack used in the auto-sampler 30 has a rectangular shape in a top view, and vials can be arranged in a matrix of n rows and m columns (12 rows and 8 columns in this example) in one sample rack.

In order to evaluate the differentiation state of a sample cell, mass spectrometry is performed in the MS unit 32 on at least one compound selected from the group consisting of, for example, putrescine, quinurenin, cystathionine, ascorbic acid, riboflavin, pyruvic acid, serine, cysteine, threonic acid, citric acid, and orotic acid as a biomarker. The method of a mass analysis device used as the MS unit 32 is not particularly limited as long as it includes an atmospheric pressure ion source. For example, a quadrupole mass analysis device, a tandem quadrupole mass analysis device, a quadrupole-time-of-flight mass analysis device, or the like can be used.

The data processing unit 4 includes functional blocks, such as, e.g., a sample information storage unit 40, a data storage unit 41, a quantitative analysis unit 42, an analysis result storage unit 43, and a result display processing unit 44. The sample information storage unit 40 stores sample information input and set for each vial in which a culture medium sample is accommodated in the preprocessing device 2, as will be described later. The data storage unit 41 stores data collected by performing analysis in the LC-MS 3. The quantitative analysis unit 42 creates an extracted ion chromatogram for each of the data obtained by targeting a particular compound, uses the data as a calibration curve created in advance, and calculates the concentration value of the compound based on the area value and the height value of the peaks observed in the chromatogram. The analysis result storage unit 43 stores a result of computation by the quantitative analysis unit 42 or the like. The result display processing unit 44 prepares a graph based on the calculated analysis result and the like, prepares a screen of a predetermined format in which the graph is arranged, and outputs the screen to the display unit 8 via the main control unit 6.

The control unit 5 includes functional blocks, such as, e.g., a preprocessing execution control unit 50, an LC-MS execution control unit 51, a display control unit 52, an input processing unit 53, a vial number management unit 54, and a setting information storage unit 55. The preprocessing execution control unit 50 controls the preprocessing operation in the preprocessing device 2. The LC-MS execution control unit 51 controls the analytical operation in the LC-MS 3. As will be described later, the display control unit 52 creates a screen for displaying the operating states in the preprocessing device 2 and LC-MS 3 and a screen for an operator to set information (sample information) of a culture medium sample used for the preprocessing device 2 or analytical conditions for each sample, and outputs the screen to the preprocessing device 2 via the display control unit 52. The input processing unit 53 executes a predetermined process in response to an input operation of the operation unit 7 by an operator. The vial number management unit 54 assigns a vial number to a vial position in each of the sample placement section 20 and the sample placement section 302 in accordance with a predetermined rule or in accordance with the manual setting by a user, and manages the information of the assignment. The setting information storage unit 55 stores sample information, analysis conditions, and the like of each culture medium sample, which are input and set by input operations, etc., of a user.

The data processing unit 4, the control unit 5, and the main control unit 6 are actually personal computers (or more sophisticated workstations), and the functions of the above-mentioned blocks can be achieved by operating one or a plurality of dedicated software installed in the computer on the computer. In this configuration, the operation unit 7 is a pointing device, such as, e.g., a keyboard or a mouse, attached to a personal computer or the like, and the display unit 8 is a display monitor.

As described above, in this system, a culture medium sample accommodated in one vial among a plurality of vials placed in the sample placement section 20 in the preprocessing device 2 is subjected to preprocessing and diluting operations and then injected into one vial among a plurality of vials placed in the sample placement section 302 of the auto-sampler 30. Therefore, in principle, a large number of vials placed in the sample placement section 20 in the preprocessing device 2 and a large number of vials placed in the sample placement section 302 in the auto-sampler 30 can be associated one-to-one. A characteristic display control is performed so that an operator can easily and accurately grasp the correspondence relationship between vials. Next, the display control will be described.

Figure 2:
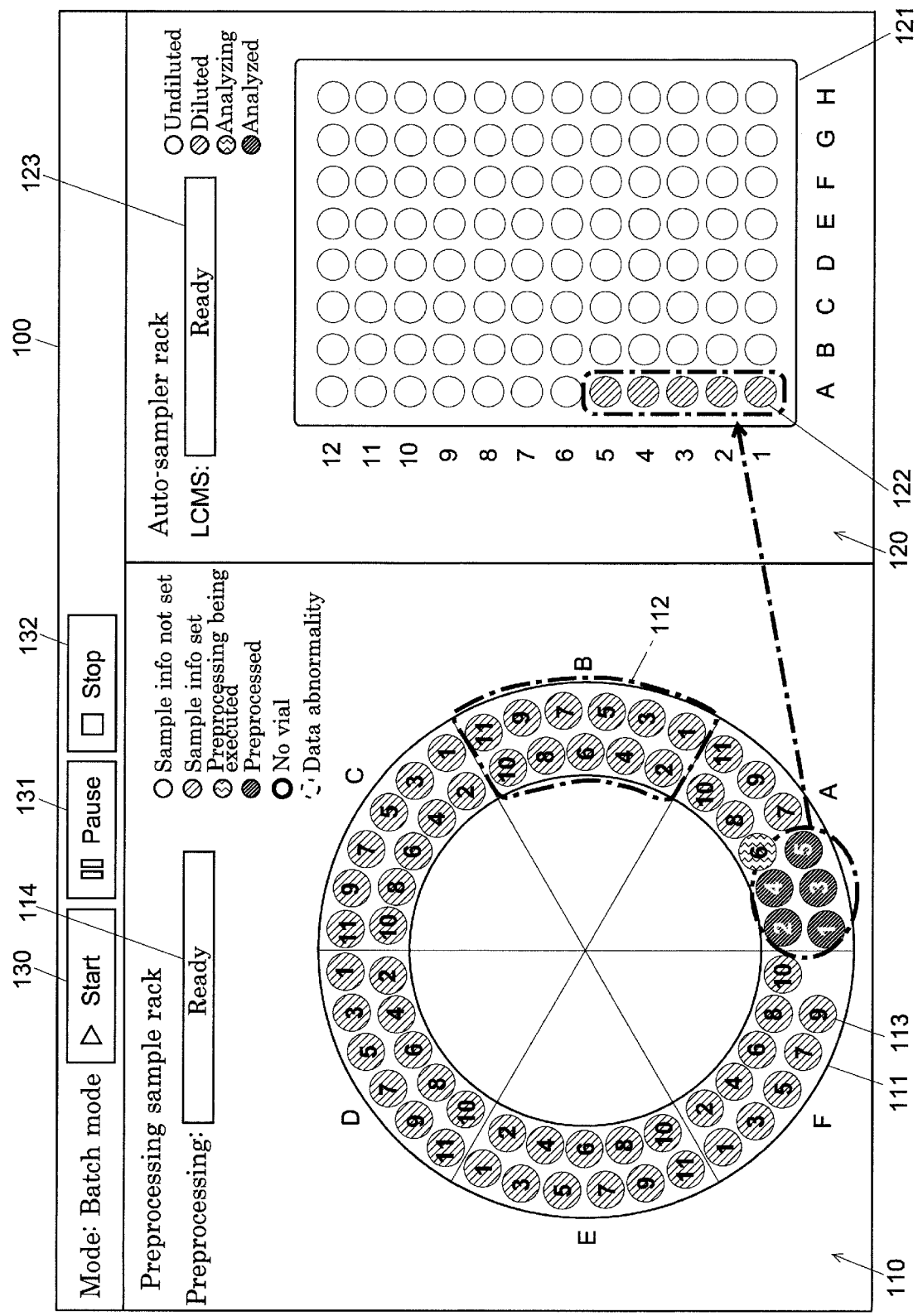
FIG. 2 is a schematic diagram showing an example of a device status display screen displayed on a display unit in the culture medium sample automatic analysis system of this example.

When an operator performs a predetermined manipulation on the operation unit 7, the display control unit 52 that received an instruction via the main control unit 6 creates a device state confirmation screen in a predetermined format and displays it on the screen of the display unit 8. FIG. 2 is a schematic diagram showing an example of a device state confirmation screen 100. This device state confirmation screen 100 is a screen for simultaneously displaying the information on the operation of the preprocessing device 2 and the operation of the LC-MS 3. That is, the device state confirmation screen 100 is generally divided into two regions on the left and right, and the left side is a preprocessing status display region 110 and the right side is an analysis status display region 120.

In the preprocessing status display region 110 of the device state confirmation screen 100, a first sample arrangement image 111 graphically showing a top view image of the sample placement section 20 in the preprocessing device 2 is displayed. This first sample arrangement image 111 is divided into six pieces of arcuate regions 112 in association with six pieces of substantially arc-shaped sample racks arranged along the circumference of the circular ring in the same manner as in the actual sample placement section 20. In each arcuate region 112, circular regions 113 corresponding to a plurality (11 pieces in this example) of respective vials are provided.

Here, as shown in FIG. 2, the letters "A", "B", "C", "D", "E", and "F" are given to the six arcuate regions 112, respectively, as region names. In addition, a plurality of circular regions 113 in each arcuate region 112 is given by numbers which are consecutive numbers of "1" to "11". All of the circular regions 113 in the first sample arrangement image 111 are identified by a vial number in which an alphabetic character showing the arcuate region 112 to which the circular region 113 belongs and a number which is a sequence number in the arcuate region 112 are combined. To the vial placed in a position corresponding to the circular region 113, its vial number is assigned as a sample container identifier. The relationship between the position of the vial and the vial number in the sample placement section 20 is managed by the vial number management unit 54.

The display color of each circular region 113 indicates the status of executing the preprocessing on the culture medium sample in the vial at the position corresponding to the circular region 113. Specifically, the execution status, etc., of preprocessing represented here includes six types of execution statuses, such as "Sample information not set" in which sample information such as the sample name has not yet been set, "Sample information set" in which preprocessing has not yet been executed although sample information has been set, "Preprocessing being executed" in which preprocessing is being executed, "Preprocessed" in which preprocessing has been completed, "No vial" indicating that a vial does not exist in the position, and "Data abnormality" in which the abnormality occurred during preprocessing. However, here, because colors cannot be represented due to the restrictions of the drawings, the execution state of preprocessing and the like are shown by the differences in filling, differences in line types indicating regions, and the like.

In the example of FIG. 2, the circular regions 113 corresponding to the five vials with vial numbers of "A1" to "A5" are in the "Preprocessed" state, and the circular region 113 corresponding to the one vial with the vial number of "A6" is in the "Preprocessing being executed" state. All other data are in the "Sample information set" state.

At the upper portion of the first sample arrangement image 111 in the preprocessing state display region 110, an operating state display section 114 that indicates the operating condition of the preprocessing device 2 is provided. In this example, "Ready" is displayed on the operating state display section 114 because preprocessing in the preprocessing device 2 is in a preprocessing completed state capable of executing the preprocessing. However, the display of the operating state display section 114 is switched such that "Suspended" or the like is displayed when the preprocessing device 2 is suspended and that "Standby" or the like is displayed when the preprocessing device is activated but the preparation has not yet been completed.

On the other hand, in the analysis state display region 120 of the device state confirmation screen 100, a second sample arrangement image 121 graphically showing the top-view image of the sample placement section 302 in the auto-sampler 30 is displayed. The second sample arrangement image 121 is provided with circular regions 122 corresponding to a plurality of vials arranged in a matrix of n rows and m columns (12 rows and 8 columns in this example) in the same manner as in the actual sample placement section 302.

Here, as shown in FIG. 2, alphabetical characters of "A", "B", "C", "D", "E", "F", "G", and "H" are assigned to the respective columns in the second sample arrangement image 121, and numbers which are sequence numbers of "1" to "12" are assigned to the respective rows. All of the circular regions 122 in the second sample arrangement image 121 are identified by a vial number in which an alphabetic character and a number are combined. To the vial at the position in the circular region 122, its vial number is given as a sample container identifier. The relationship between the vial position and the vial number in the sample placement section 302 is also managed by the vial number management unit 54.

The display color of each circular region 122 indicates the status of the diluting operation in the auto-sampler 30 for a preprocessed and diluted culture medium sample in a vial at a position corresponding to the circular region 122, and the status of performing the analysis in the LC unit 31 and the MS unit 32, etc. Specifically, the dilution operation and the execution state of the analysis shown here are four types of "Undiluted" in which the dilution processing has not yet been executed, "Diluted" in which the measurement has not been performed although the dilution processing has been completed, "Analyzing" in which the analysis is being executed, and "Analyzed" in which the analysis has been completed. Of course, here, instead of colors, the dilution operation, the execution state of the analysis, and the like are shown by the difference in filling and the like.

In the example of FIG. 2, the circular regions 122 corresponding to the five vials with the sample numbers of "A1" to "A5" are in the "Diluted" state. The circular regions 122 corresponding to all other vials is in the "Undiluted" state. As described above, in this system, since the diluted culture medium sample is injected into each vial, it means that a culture medium sample has not yet been injected into the vial at a position in which the circular region 122 is in the "Undiluted" state.

An operation status display section 123 indicating the operating states of LC unit 31 and MS unit 32 is provided on the upper portion of the second sample arrangement image 121 in the analysis status display region 120. In this example, "Ready" is displayed on operation status display section 123 because LC unit 31 and MS unit 32 are ready for operation, but operation status display section 123 is switched between "Stopped" when, for example, LC unit 31 and MS unit 32 are stopped, and "Ready" when activated and not yet ready.

At the top portion of the device state confirmation screen 100, a start (Start) button 130 operated when the analysis is started, a pause (Pause) button 131 operated when the analysis is paused, and a stop (Stop) button 132 operated when the analysis is stopped are arranged. After selecting an analysis method registered in advance, the analyst can instruct the start of a series of analyses including preprocessing by clicking the start button 130. Note that, FIG. 2 shows that the start button 130 has been operated and the analysis is in progress.

As described above, the vial number management unit 54 manages the relationship between the position and the vial number of the vial placed in the sample placement section 20 of the preprocessing device 2, and also manages the relationship between the vial and the vial number placed in the sample placement section 302 of the auto-sampler 30. Under this control, the vial in the sample placement section 20 and the vial in the sample placement section 302 are associated so that the sample after preprocessing of a vial in the sample placement section 302 of a vial of a vial number placed in the sample placement section 20 of the preprocessing device 2 (actually, a further diluted sample) is dispensed into a vial of the same vial number placed in the sample placement section 302 of the auto-sampler 30. Therefore, in the vial of the position corresponding to the region having the same vial number on the first sample arrangement image 111 and on the second sample arrangement image 121 in the device state confirmation screen 100, it is ensured that the sample from the same culture medium sample is accommodated. Thereby, the operator can easily grasp on the display whether or not the same sample as the sample in the vial placed in one sample placement section 20 or 302 (whether or not preprocessing or dilution has been performed is different) is in a vial placed in the other sample placement section 302 or 20.

Further, it is possible to easily grasp the culture medium sample in a vial placed in each sample placement section 20 and 302 is in which stage of preprocessing or analysis on the display. For example, as shown by a dot-dash line in FIG. 2, it is possible to easily recognize by the second sample arrangement image 121 that preprocessing in the preprocessing device 2 has been completed for the culture medium samples in the five vials having the vial numbers of "A1" to "A5" in the first sample arrangement image 111 and they have been transferred to the auto-sampler 30 and have been diluted.

In the example shown in FIG. 2, sample information has been set for all vials placed in the sample placement section 20 of the preprocessing device 2, and the analysis has been started. On the other hand, before starting the analysis, the operator inputs and sets the sample information about the culture medium sample in each vial and the analysis condition for analyzing each culture medium sample by the LC-MS 4 for all vials placed in the sample placement section 20 of the preprocessing device 2. The sample information includes the seeding date and time, the culture name, the culture plate number, the harvest date and time, etc. The analysis method including the set sample information and the analysis condition is stored in the setting information storage unit 55 in association with the vial number. In one approach, the sample information can be set as follows.

Figure 3:
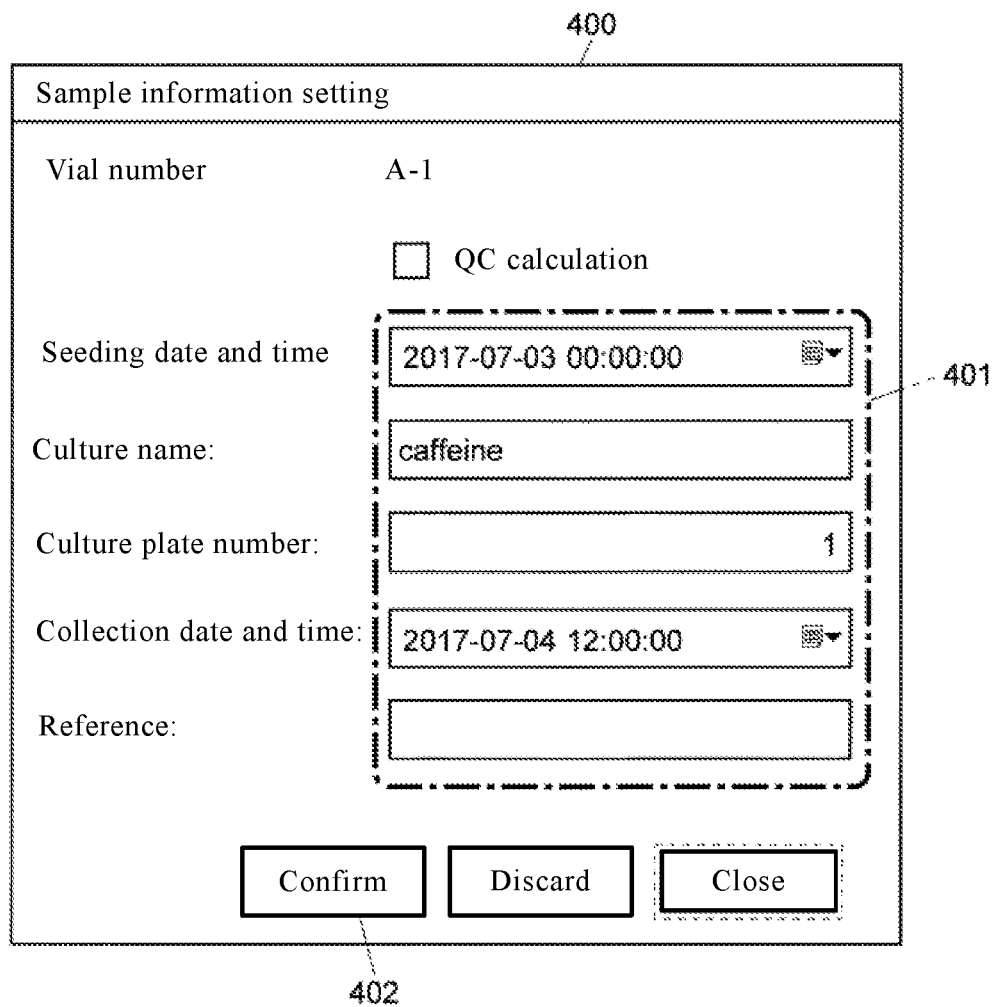
FIG. 3 is a diagram showing an example of a sample information setting screen in the culture medium sample automatic analysis system of this example.

When there is a vial whose sample information has not yet been set in the first sample arrangement image 111 on the device state confirmation screen 100 as shown in FIG. 2, the operator clicks a circular region 113 corresponding to a vial for which sample information is to be set with a pointing device included in the operation unit 7. Then, the display control unit 52 receives the operation, opens a new sample information setting screen 400 corresponding to the instructed vial number as shown in FIG. 3, and displays the newly opened sample information setting screen 400 on the screen of the display unit 8. FIG. 3 shows the case where a circular region 113 to which a vial number "A1" is assigned is instructed.

In this sample information setting screen 400, a text box 401 for inputting sample information, such as, e.g., seeding date and time, a culture name, a culture plate number, collection date and time, and a reference, is arranged. The reference is a value that is used as required when calculating and/or processing the analytical result, which will be described later, and can be an arbitrary value of, for example, the number of cells in the original culture vessel from which the culture medium sample was obtained, the lactate value (the quantity of substances produced when sugar is consumed), the concentration of bacteria, the absorbance of the culture solution, or the like, which is obtained by measuring or observing the results by another device not included in this system.

The operator inputs or selects appropriate information on the above-described items relating to sample information, and then clicks on the confirm button 402. Then, the input processing unit 53 receives this operation, determines the sample information for the vial number at that time, creates a sample information file including the sample information for each vial number, and stores the file in the setting information storage unit 55.

In the above procedures, the operator needs to input and set sample information for each vial, but it is also possible to collectively set sample information corresponding to a plurality of vials by creating a table in which sample information, such as, e.g., a seeding date and time, a culture name, a culture plate number, a collection date and time, and the like, is grouped in advance for a plurality of vials, i.e., a culture medium sample, and selecting a plurality of vials for which sample information has not been set and then selecting corresponding plurality of sample information on the above table.

Figure 4:
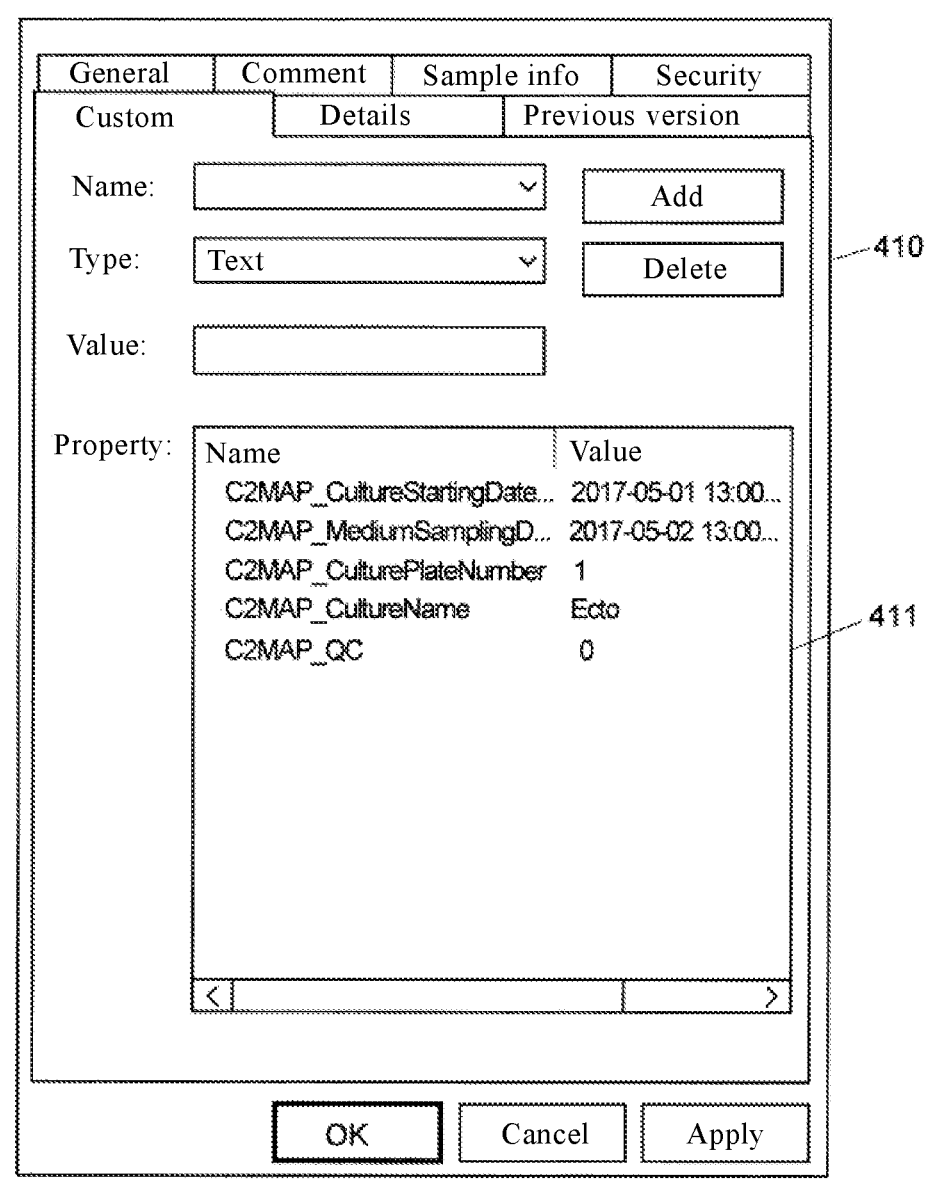

As described above, the input processing unit 53 stores a sample information file including sample information in the setting information storage unit 55 for each vial, and at this time, the information of each item of the sample information is automatically registered in the custom property which is one of attribute information of the file. FIG. 4 is a diagram illustrating an example of a status in which sample information has been automatically registered in the custom property 411 on the file property dialogue screen 410. In this case, texts are set as the types of values of custom properties, and information on the seeding date and time, the collection date and time, the culture name, the culture plate number, and the QC value is registered as values corresponding to the names of "C2MAP_CultureStartingDate", "C2MAP_CultureSamplingDate", "C2MAP_CulturePlateNumber", "C2MAP_CultureName", and "C2MAP_QC", respectively.

As described above, the file including the sample information set for each vial in the control unit 5 is transferred to the data processing unit 4 at an appropriate time and stored in the sample information storage unit 40.

The data format of the file in which sample information is stored may vary from a manufacturer to a manufacturer of this system, but file properties can be shared on the same operating system base, e.g., Windows (registered trademark). Thus, for example, even when the manufacturer of the preprocessing device 2 constituting this system is different from the manufacturer of the LC-MS 3, and the data of the file in which sample information has been stored cannot be read data by the data processing unit 4 that processes data by the LC-MS 3, the sample information can be acquired using the properties of the file.

Next, the display mode of the analysis result after the analysis for a large number of culture medium samples is performed in this system will be described.

As described above, the data collected by analyzing a large number of culture medium samples by the LC-MS 3 is stored in the data storage unit 41. The quantitative analysis unit 42 uses the data to generate an extracted ion chromatogram for one or a plurality of given compounds per vial and calculates the area values of the peaks corresponding to the compounds. Further, a concentration value is calculated from the peak area value by referring to a calibration curve prepared in advance. Thereby, the peak area value and the concentration value of one or a plurality of compounds are obtained for each vial, that is, for each culture medium sample, and they are stored in the analysis result storage unit 43 as one file.

At this time, the file of the analytical result for each sample stored in the analysis result storage unit 43 is correlated with the file whose data is sample information of the same culture medium sample stored in the sample information storage unit 40. The data file of each sample stored in the data storage unit 41 is also correlated with the file of the sample information. As a result, for example, the analysis result file and/or the data file of the sample can be easily accessed from the sample information, and conversely, the sample information of the sample can be easily acquired from the analysis result file and/or the data file. As a result, the traceability related to the analysis can be appropriately managed.

Usually, in the culture medium analysis in which this system is used, the culture supernatant in one culture vessel is continuously analyzed, for example, every day at the same time until the culture is completed, in order to evaluate the differentiation status of sample cells in culture. Therefore, culture medium samples to which the same culture name is assigned are analyzed every day, and the data files and the analytical result files are created and stored, respectively. Since the amounts of compounds in culture medium samples derived from the same culture vessel (e.g. metabolites by cells) vary from day to day, observing this temporal change is crucial in the cell assessment. In this system, graphs based on analytical results are displayed in association with sample information in the following manner.

Figure 5:
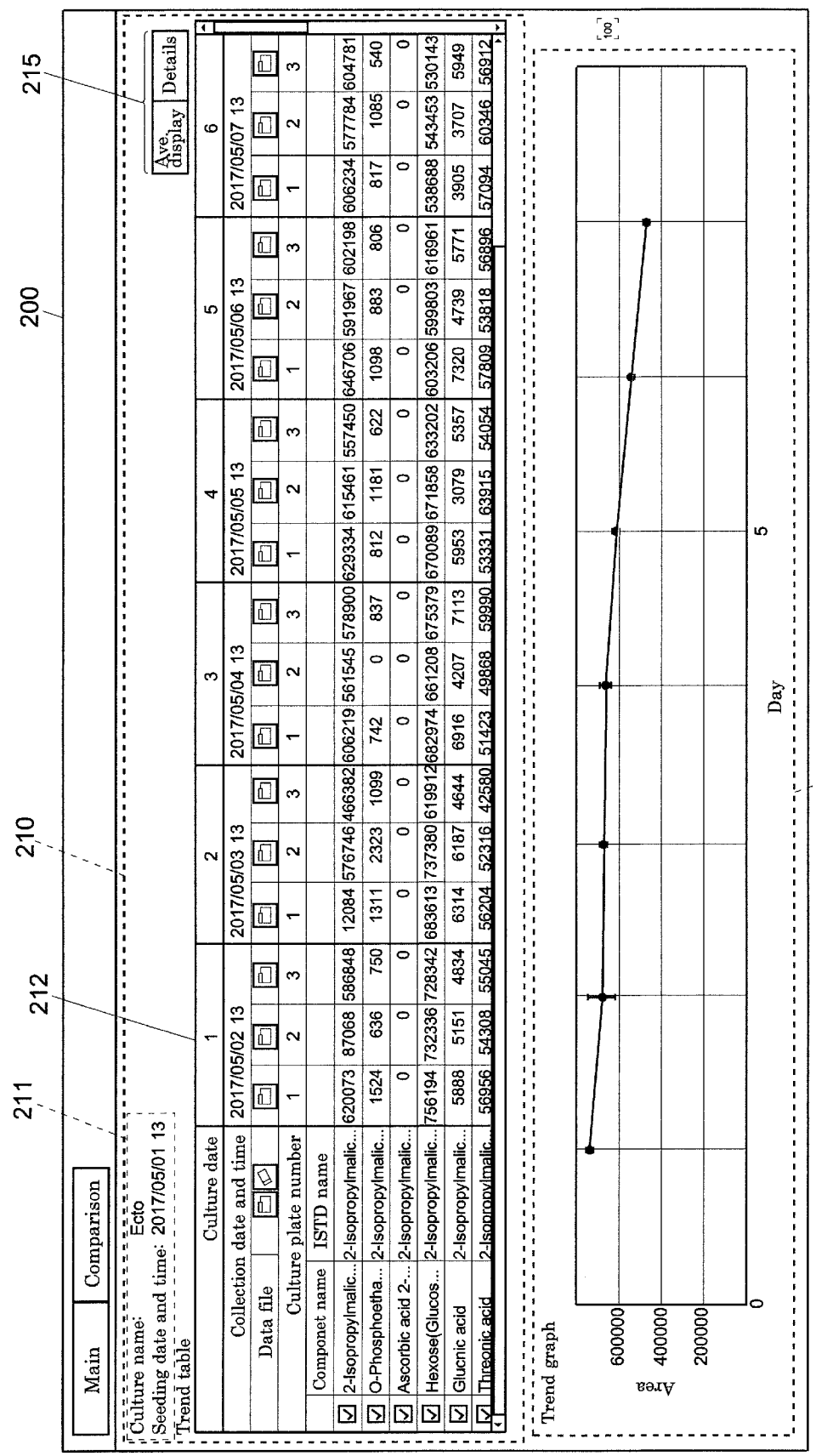
FIG. 5 is a diagram showing an example of an analysis result display screen (main screen) in the culture medium sample automatic analysis system of this example.
Figure 6:
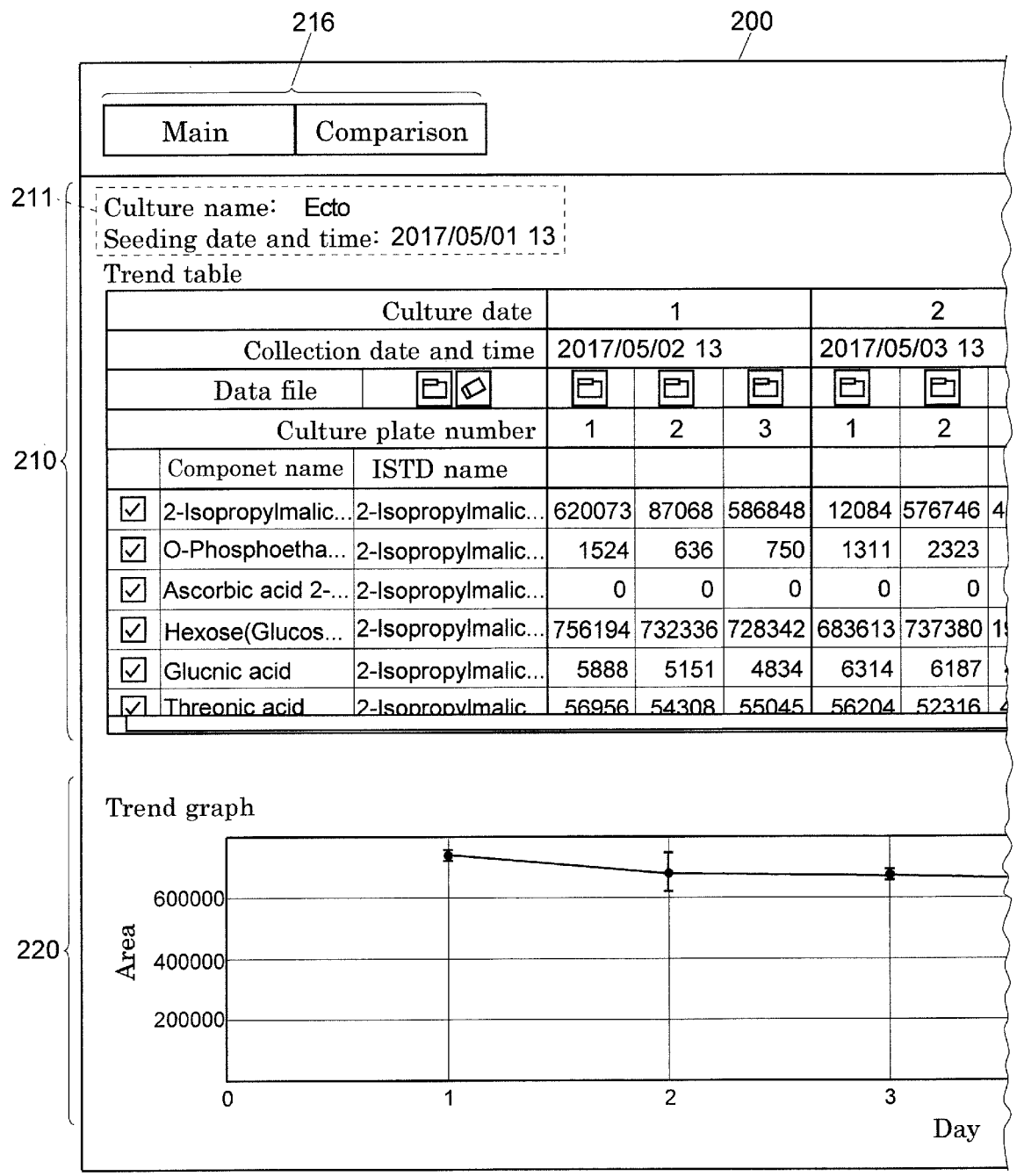
FIG. 6 is a diagram showing a left part of the analysis result display screen shown in FIG. 5.

That is, when an operator performs a predetermined manipulation after designating a culture name or the like in the operation unit 7, the result display processing unit 44 reads the file of the sample information corresponding to the designated information and the analytical result file from the sample information storage unit 40 and the analysis result storage unit 43, creates a main analysis result display screen 200 as shown in FIG. 5 and FIG. 6 based on the data in the file and displays the screen on the display unit 8. FIG. 5 is a diagram showing the entire main analysis result display screen 200, and FIG. 6 is a diagram showing a left part of the main analysis result display screen 200. The main analysis result display screen 200 is divided roughly into two parts upward and downward, and a table display region 210 is provided upward and a graph display region 220 is provided downward.

In the upper left part of the table display region 210, a sample information display region 211 for displaying a culture name as sample information and a seeding date and time is provided, and a trend table 212 is disposed below the sample information display region 211. The trend table 212 is a table in which the types of compounds (metabolites) to be analyzed are arranged in the vertical direction, and culture plate numbers for the culture date (number of days elapsed from the initiation of culture) and the collection date and time are arranged in the horizontal direction. In this example, the number of culture vessels (culture plates) cultured under the same condition is three, so the culture plate number is only 1 to 3, but this number can be further increased.

In the respective cells of the trend table 212, a quantitative value for one culture plate number of a certain type of compound on a certain culture date is displayed. The quantitative value described here is a peak area value, the area ratio to a peak area value under a specific condition (for example, the area ratio when the area value on the first day of the collection date and time is set to 1), a concentration value, the concentration ratio to a concentration value under a specific condition (for example, the concentration ratio when a concentration value on the first day of the collection date and time is set to 1), or any of the calculated values obtained by dividing these values by the above-mentioned reference value. Which value is to be displayed as the quantitative value can be appropriately selected by an operator in another setting screen, but in any case, the analytical result calculated for each compound by the quantitative analysis unit 42 is displayed here.

A detailed mode/average display mode selection button 215 is provided at the upper right portion of the table display region 210. FIG. 5 and FIG. 6 show a state in which the detailed mode is selected by the button 215, and in this state, all the results of three samples having different culture plate numbers at the same collection date and time are displayed. On the other hand, when the average display mode is selected by the detailed mode/average display mode selection button 215, the result display processing unit 44 averages the results of three samples having different culture plate numbers at the same collection date and time for each compound, and displays the average values in the trend table 212. Even if cultured under the same conditions, it is inevitable that a difference occurs in the cell proliferation and the like, and the results of the three samples at the same collection date and time have a certain degree of discrepancy. Therefore, usually, only the average value is confirmed by the average display mode. However, if the result is questionable, the presence or absence of abnormal values can be confirmed by confirming the individual peak area value and/or the concentration value by selecting the detailed display mode.

In the graph display region 220 of the main analysis result display screen 200, a graph (trend graph) indicating a change in peak area value or the like of one compound selected in the trend table 212 is displayed. When the operator specifies a compound whose trend graph is desired to be confirmed by the operation unit 7 on the trend table 212, the result display processing unit 44 collects the analytical results for the indicated compound and generates the trend graph to update the display in the graph display region 220. In the example of FIG. 5, "Hexose (Glucose)" in the fourth line of the trend table 212 is selected, and the trend graph indicating the change in the peak area value with respect thereto is displayed. The value on the graph is an average for three samples with different culture plate numbers at the same collection date and time, and the variations in the value are indicated by error bars. The value used for this error bar display can be selected by the operator from among variances, standard deviations, etc. in a different setting screen.

When the variation of the error bar displayed value is too large, there is a high possibility that some abnormality has occurred. Therefore, a threshold value for an error may be specified by a different setting screen by an operator, and when the error exceeds this threshold value, an operator may be warned that the degree of the error is abnormal by displaying the error bar in a display color different from the normal display color or the like.

In the main analysis result display screen 200, only a trend graph for one specified culture name can be confirmed. However, in cases where it is desired to compare the results of a plurality of culture medium samples different in culture name, the operator selects the comparison mode with the main mode/comparison mode selection button 216 displayed at the uppermost portion of the main analysis result display screen 200. Then, the result display processing unit 44 displays a comparison analysis result display screen 300 as shown in FIG. 7 on the display unit 8.

Figure 7:
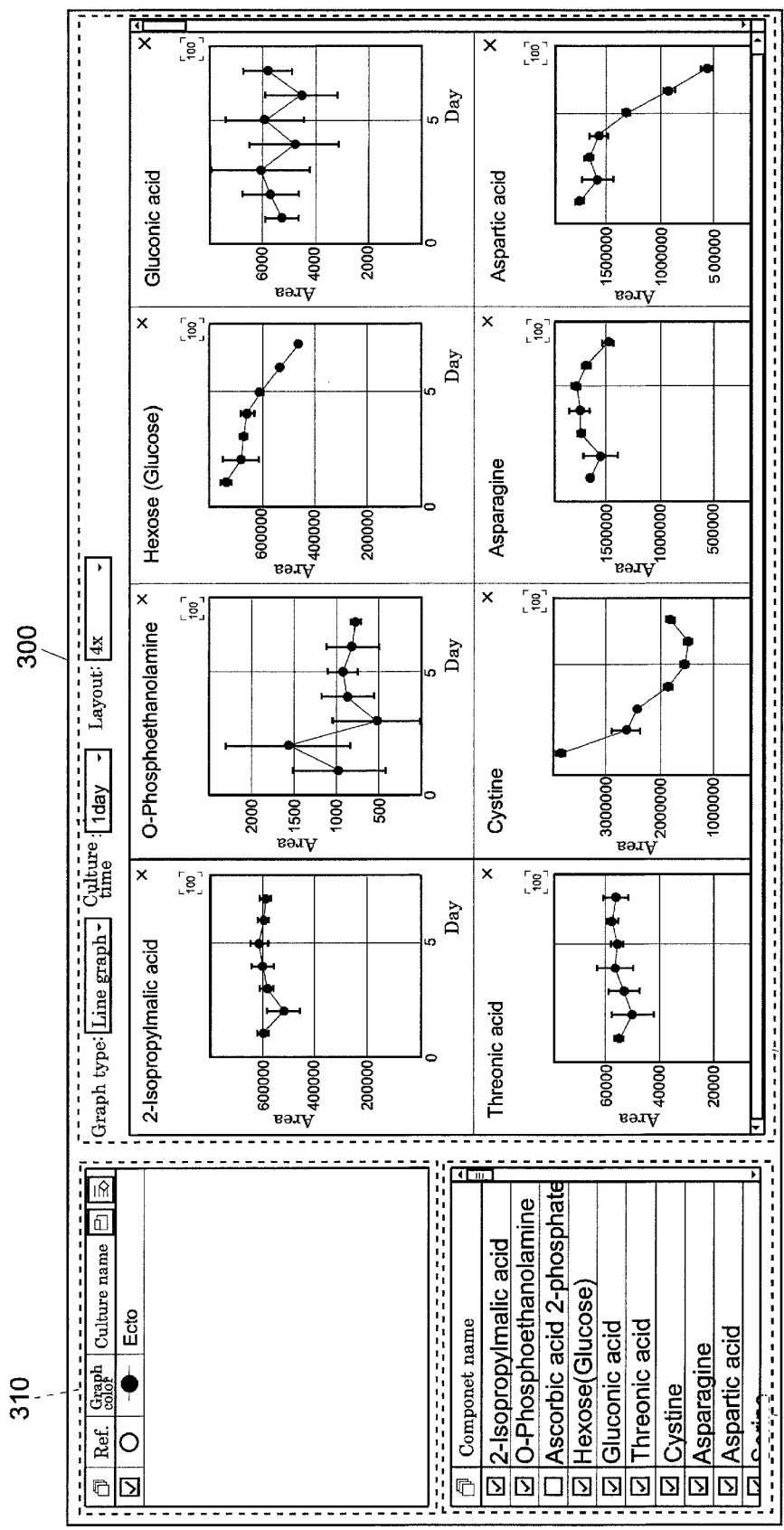
FIG. 7 is a diagram showing an example of an analysis result display screen (comparison screen) in the culture medium sample automatic analysis system of this example.
Figure 8:
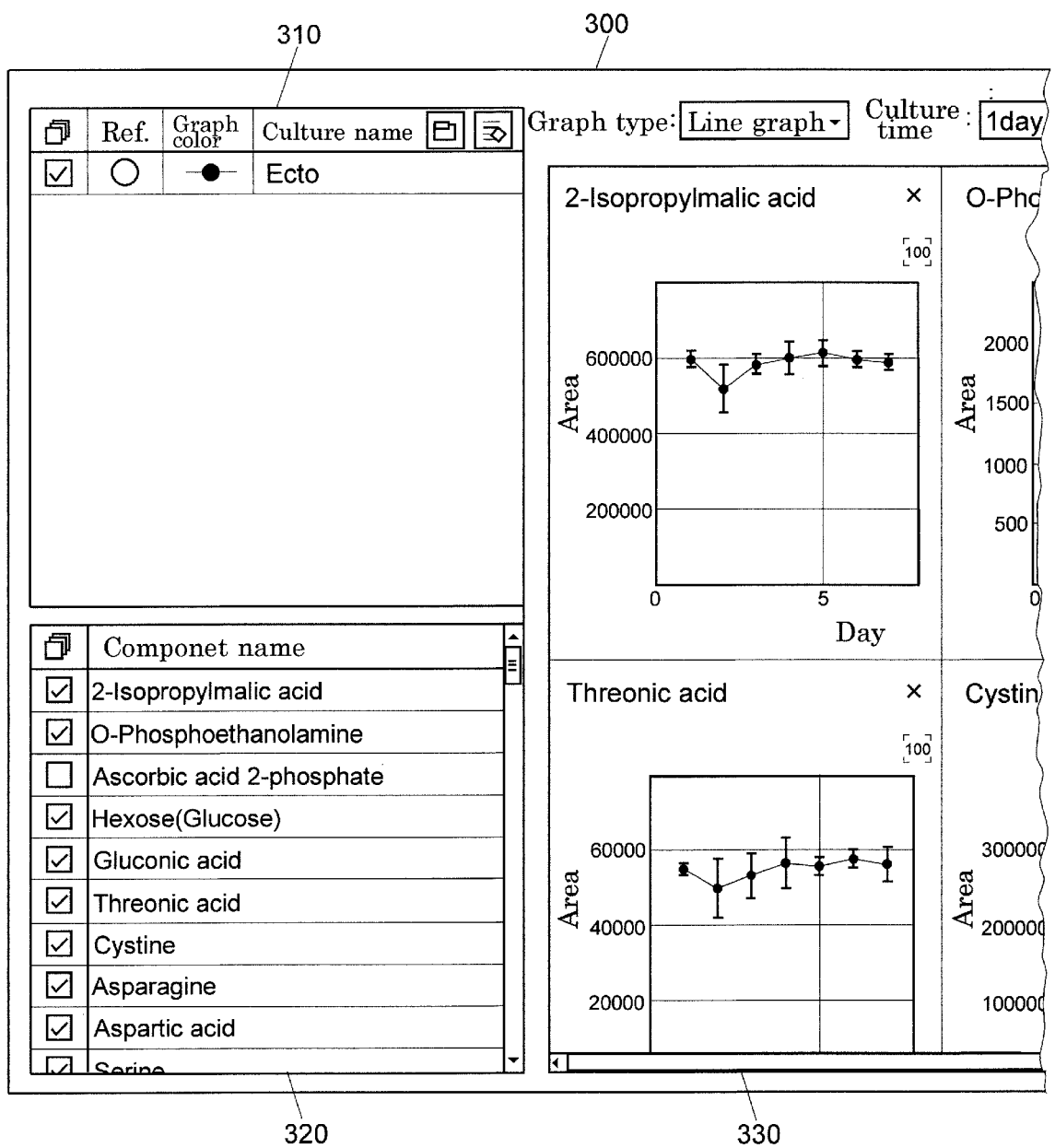
FIG. 8 is a diagram showing a left part of the analysis result display screen shown in FIG. 7.

FIG. 7 is a diagram showing the entire comparison analysis result display screen 300, and FIG. 8 is a diagram showing a left side part of the comparison analysis result display screen 300. The comparison analysis result display screen 300 is generally divided into three regions. A sample type table display region 310 is provided at the upper left, a compound table display region 320 is provided at the lower left, and a graph display region 330 is provided at the right. A sample type table having one culture name as one line is displayed in the sample type table display region 310, and a compound table having one compound as one line is displayed in the compound table display region 320. A check box is provided in each row of the sample type table and the compound table, and a trend graph which is an analyzed result obtained by checking the check box is displayed in the graph display region 330.

In the example of FIG. 7 and FIG. 8, trend graphs of the compounds other than the ascorbic acid 2-phosphate for the culture medium sample whose culture name is "Ecto" is displayed in the graph display region 330. The trend graph per se is the same as that displayed in the graph display region 220 of the main analysis result display screen 200, and averages and error bars, such as the peak area values and the concentration values, are displayed for each collection day. This makes it possible to easily compare temporal changes such as peak area values of different compounds.

Figure 9:
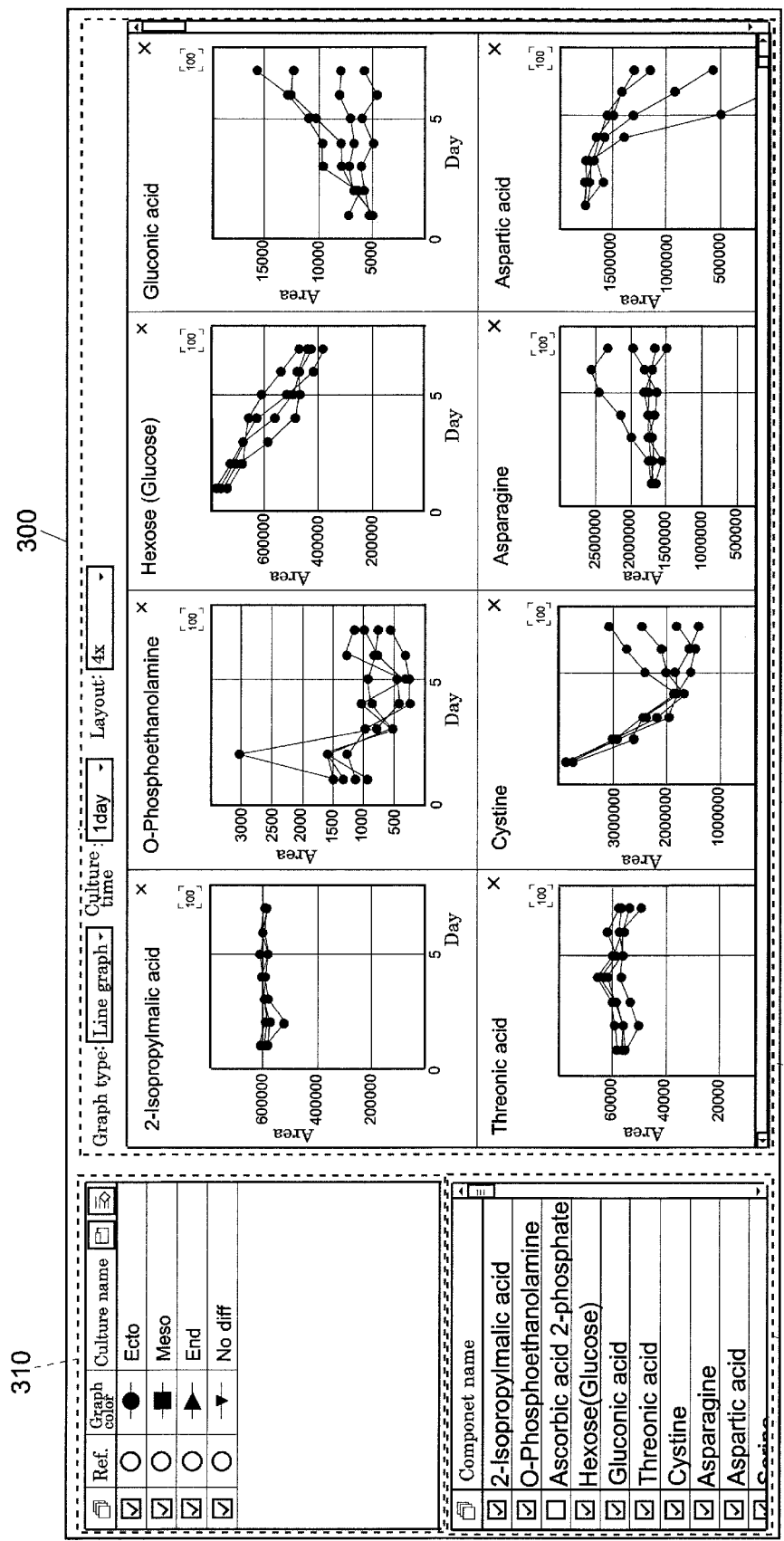
FIG. 9 is a diagram showing an example of an analysis result display screen (comparison screen) in the culture medium sample automatic analysis system of this example.
Figure 10:
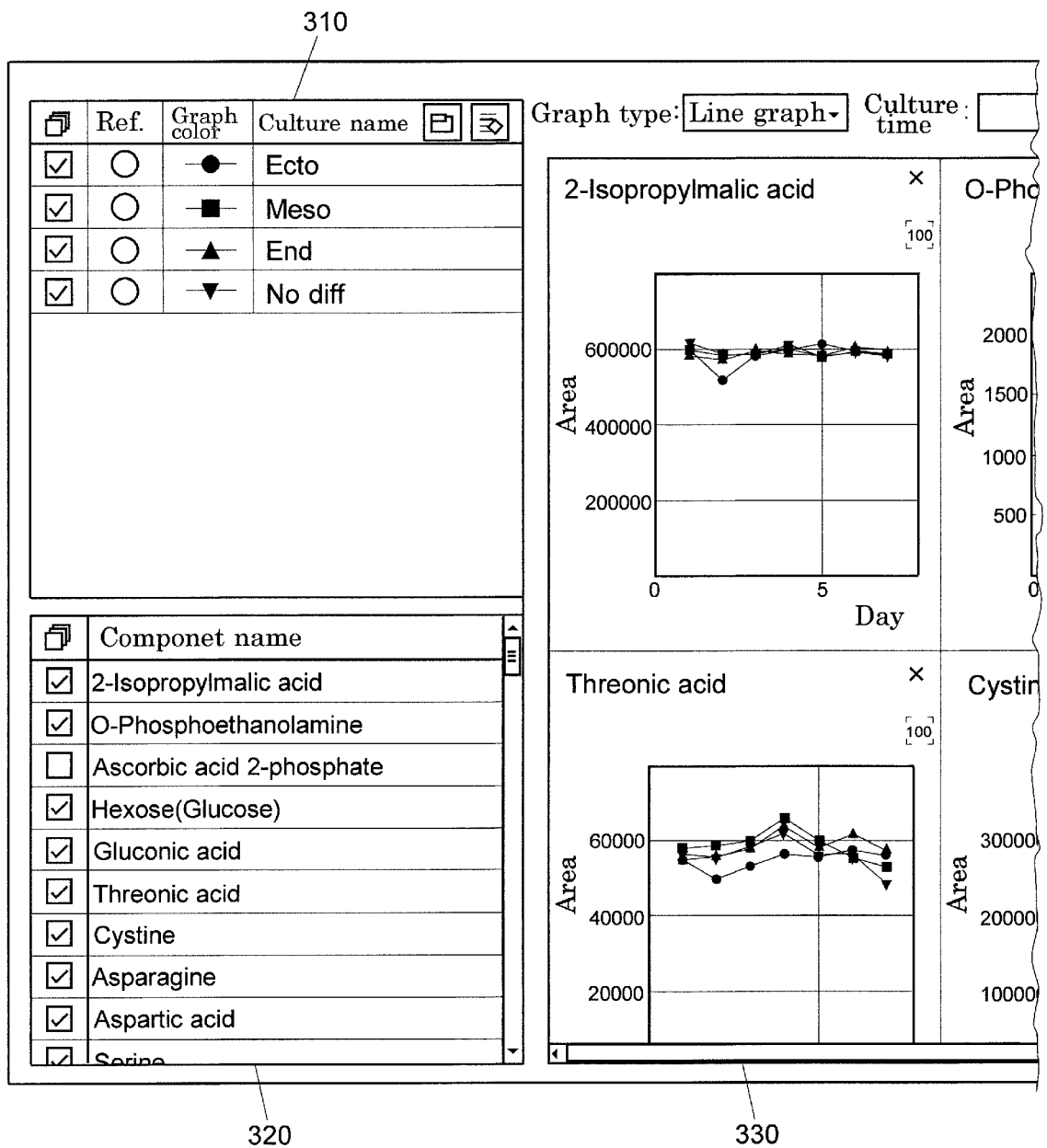
FIG. 10 is a diagram showing a left part of the analysis result display screen shown in FIG. 9.

It is also possible to compare the analytical results of culture medium samples, which are different culture names, in the comparison analysis result display screen 300. That is, when an operator designates a plurality of culture names to be compared in the another setting screen, the result display processing unit 44 displays a comparison analysis result display screen 300 as shown in FIG. 9 and FIG. 10 on the display unit 8. FIG. 9 is a diagram showing the entire comparison analysis result display screen 300, and FIG. 10 is a diagram showing a left side portion of the comparison analysis result display screen 300. At this time, a sample type table in which a plurality of designated culture names is listed is displayed in the sample type table display region 310. Different graph colors are assigned to each culture name. Note that, here, since the color cannot be shown, the shape of plot points on the graph is differentiated.

Then, a trend graph in which line graphs corresponding to different samples having different culture names are superimposed is displayed in the graph display region 330. In the examples of FIG. 9 and FIG. 10, trend graphs of compounds other than Ascorbic acid 2-phosphate for four types of culture medium samples whose culture names are "Ecto", "Meso", "End", and "No diff" are displayed in the graph display region 330. This makes it possible to easily compare changes in quantitative values of the same compound in different cultured cells.

Figure 11:
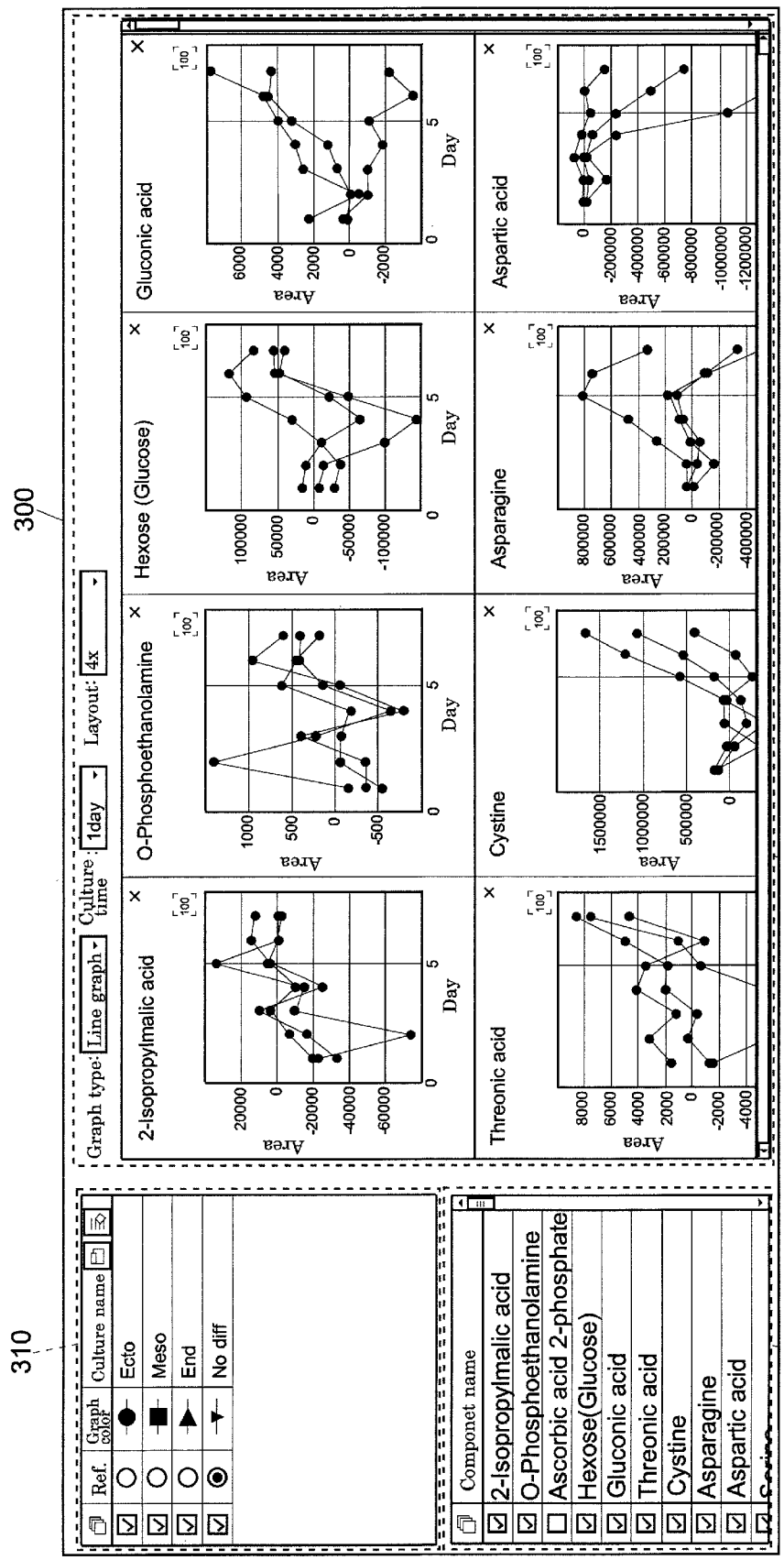
FIG. 11 is a diagram showing an example of an analysis result display screen (comparison screen) in the culture medium sample automatic analysis system of this example.
Figure 12:
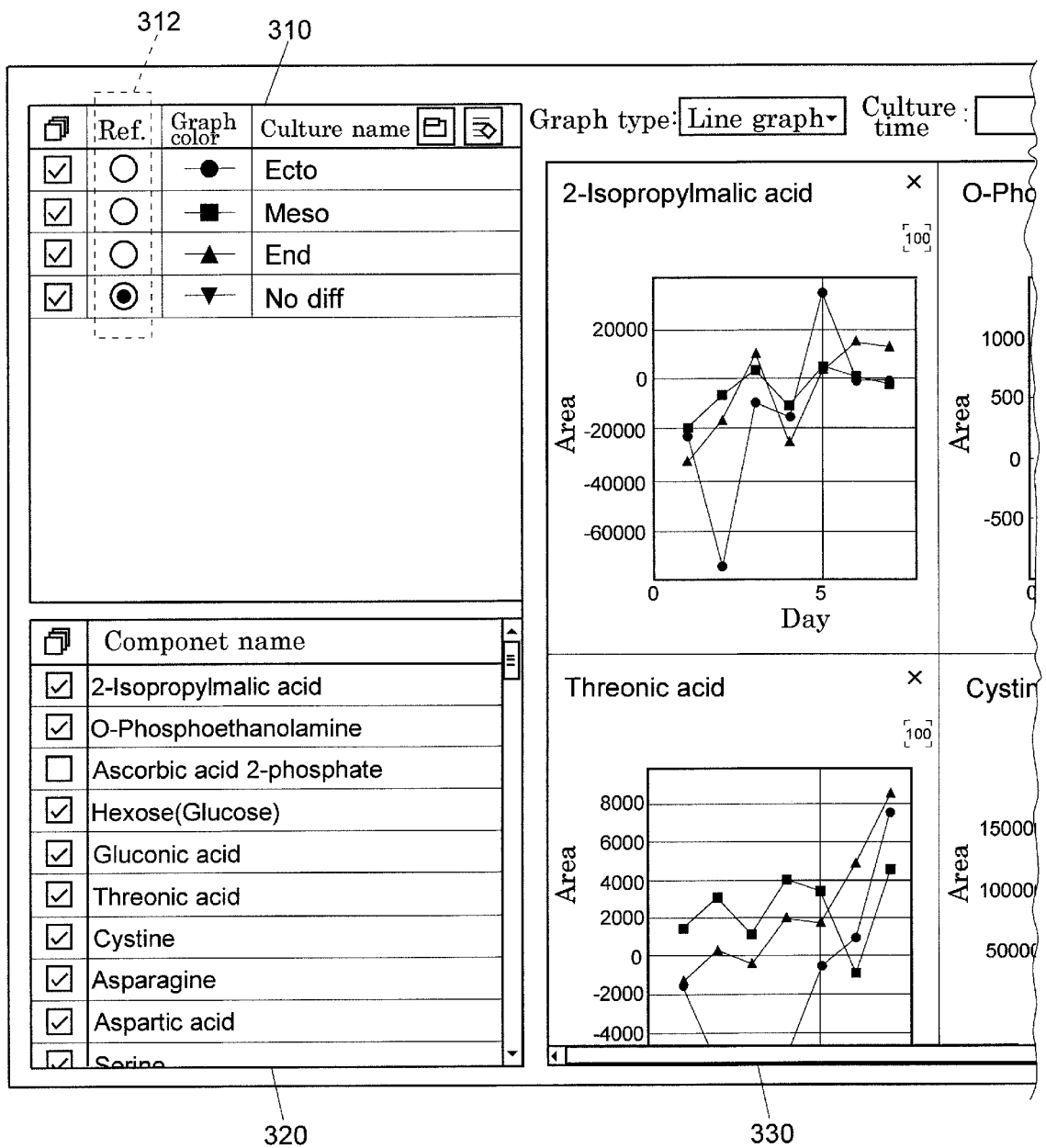
FIG. 12 is a diagram showing a left part of the analysis result display screen shown in FIG. 11.

Furthermore, any one of a plurality of culture medium samples may be used as a reference, and differences between the analysis result of the reference and other analysis results may be displayed. That is, as shown in FIG. 11 and FIG. 12, when an operator checks the reference radio button 312 of a row corresponding to one sample to be used as a reference on the sample type table displayed in the sample type table display region 310, the result display processing unit 44 calculates, for each compound, the difference between the peak area value or concentration value in the reference sample and the peak area value or concentration value in the other sample, and creates a trend graph indicating the temporal change of the difference. Then, a trend graph is displayed on the graph display region 330.

In the examples of FIG. 11 and FIG. 12, the culture medium sample whose culture name is "No diff" is used as a reference, and a trend graph of compounds other than Ascorbic acid 2-phosphate for the other three types of samples is displayed in the graph display region 330. In this trend graph, it is possible to more intuitively grasp the change in the difference between the quantitation value and the reference value.

It should be noted that the above examples are examples of the present invention, and it is needless to say that the scope of the present invention may be appropriately changed, modified, or added to encompass the claims.

For example, in the system of the above examples, the number of vials mountable in the sample placement section 20 and 302 may be changed as appropriate, and the shape of the rack on which vials are mounted in the sample placement section 20 and 302 may also be changed as appropriate. In addition, the method of applying the vial number can be changed as appropriate.

Although the above examples are directed to a system of analyzing a compound such as a metabolite contained in a culture medium sample by an LC-MS, a compound in a sample derived from another living body of a culture medium sample may be analyzed. The analysis device is not limited to an LC-MS, and may be a GC-MS, or may be an analysis device, such as, e.g., another optical analysis device. As described above, the preprocessing by the preprocessing device is not limited to removing proteins or other undesirable components and may be various preprocessing. Further, in the system of the above examples, the dilution of a sample is carried out by an auto-sampler in an LC-MS, but the dilution may be carried out by a preprocessing device.

DESCRIPTION OF SYMBOLS

1 . . . Culturing device
2 . . . Preprocessing device
20 . . . Sample placement section
21 . . . Preprocessing execution unit
22 . . . Sample delivery unit
3 . . . LC-MS
30 . . . Auto-sampler
301 . . . Sample dilution unit
302 . . . Sample placement section
303 . . . Sampling unit
31 . . . LC unit
32 . . . MS unit
4 . . . Data processing unit
40 . . . Sample information storage unit
41 . . . Data storage unit
42 . . . Quantitative analysis unit
43 . . . Analysis result storage unit
44 . . . Result display processing unit
5 . . . Control unit
50 . . . Preprocessing execution control unit
51 . . . LC-MS execution control unit
52 . . . Display control unit
53 . . . Input processing unit
54 . . . Vial number management unit
55 . . . Setting information storage unit
6 . . . Main control unit
7 . . . Operation unit
8 . . . Display unit
100 . . . Device state confirmation screen
110 . . . Preprocessing status display region
111 . . . First sample arrangement image
112 . . . Arcuate region
113, 122 . . . circular region
120 . . . Analysis status display region
121 . . . Second sample arrangement image
114, 123 . . . operation status display section
130 . . . Start button
131 . . . Pause button
132 . . . Stop button

The invention claimed is:

1. A biological sample automatic analysis system in which predetermined preprocessing is performed on a sample derived from a living organism and then a predetermined analysis is performed on a preprocessed sample which is the sample that has been subjected to the preprocessing, the system comprising:
   a) a preprocessing device having a first sample placement section for placing a plurality of sample containers each accommodating a sample, the preprocessing device being configured to perform preprocessing on the samples in the sample containers placed in the first sample placement section;

b) an analysis device having a second sample placement section for placing a plurality of sample containers each accommodating a respective preprocessed sample which is a sample that has been subjected to the preprocessing by the preprocessing device, the analysis device being configured to perform an analysis on the preprocessed samples in the sample container placed in the second sample placement section;

c) a sample information acquisition unit configured to acquire sample information related to the sample accommodated in each sample container placed in the first sample placement section in association with a sample container identifier assigned to each sample container according to a placement position in the first sample placement section;

d) a sample container identifier management unit configured to manage a sample container identifier assigned to each sample container depending on a placement position in the first sample placement section and to manage a sample container identifier assigned to each sample container depending on a placement position in the second sample placement section, so that a preprocessed sample originating from a sample accommodated in a first sample container among the plurality of sample containers placed in the first sample placement section is dispensed into a second sample container among the plurality of sample containers placed in the second sample placement section, the second sample container having a sample container identifier the same as a sample container identifier of the first sample container, and each sample container placed in the first sample placement section is associated with a respective sample container placed in the second sample placement section; and e) an analysis result storage processing unit configured to receive sample information obtained by the sample information acquisition unit and store an analysis result obtained by an analysis by the analysis device on a sample in a sample container to which an arbitrary sample container identifier has been assigned, with or in association with sample information corresponding to the sample container identifier, in accordance with a management by the sample container identifier management unit.

2. The biological sample automatic analysis system as recited in claim 1, further comprising:

a display processing unit configured to display the analysis result stored by the analysis result storage processing unit and the sample information corresponding to the analysis result on a same screen of a display unit.

3. The biological sample automatic analysis system as recited in claim 2, wherein the analysis device includes a liquid chromatograph mass spectrometer or a gas chromatograph mass spectrometer, and the analysis result includes a quantitative value for one or a plurality of compounds as a result of performing a data-based quantitative analysis obtained by the liquid chromatograph mass spectrometer or the gas chromatograph mass spectrometer.

4. The biological sample automatic analysis system as recited in claim 2, wherein the biological sample is a culture medium sample derived from a culture medium in which a sample cell is cultured, and the sample information includes a culture name for specifying the culture medium, seeding date and time of cells, and collection date and time of the culture medium sample.

5. The biological sample automatic analysis system as recited in claim 1, wherein the sample information acquisition unit is configured to create a file for storing the sample information associated with the sample container identifier, and register the sample information in a custom property of the file.

6. The biological sample automatic analysis system as recited in claim 2, wherein the sample information acquisition unit is configured to create a file for storing the sample information associated with the sample container identifier, and register the sample information in a custom property of the file.

7. The biological sample automatic analysis system as recited in claim 3, wherein the sample information acquisition unit is configured to create a file for storing the sample information associated with the sample container identifier, and register the sample information in a custom property of the file.

8. The biological sample automatic analysis system as recited in claim 4, wherein the sample information acquisition unit is configured to create a file for storing the sample information associated with the sample container identifier, and register the sample information in a custom property of the file.

* * * * *